United States Patent
Shin (10) Patent No.: US 11,246,744 B2
(45) Date of Patent: Feb. 15, 2022

(54) DEVICE FOR MOVING LOWER JAW FORWARD

(71) Applicant: SEOUL NATIONAL UNIVERSITY R&DB FOUNDATION, Seoul (KR)

(72) Inventor: Hyun-Woo Shin, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 536 days.

(21) Appl. No.: 15/952,326

(22) Filed: Apr. 13, 2018

(65) Prior Publication Data
US 2018/0228644 A1 Aug. 16, 2018

Related U.S. Application Data

(63) Continuation of application No. PCT/KR2016/009897, filed on Sep. 5, 2016.

(30) Foreign Application Priority Data

Oct. 13, 2015 (KR) .......................... 10-2015-0142680

(51) Int. Cl.
*A61F 5/56* (2006.01)
*A61B 5/00* (2006.01)
(Continued)

(52) U.S. Cl.
CPC ............ *A61F 5/566* (2013.01); *A61B 5/1116* (2013.01); *A61B 5/4809* (2013.01);
(Continued)

(58) Field of Classification Search
CPC ........ A61H 2205/026; A61H 2205/563; A61H 1/00; A61H 2201/12–1246;
(Continued)

(56) References Cited

U.S. PATENT DOCUMENTS 2,587,528 A * 2/1952 Robinson ............... A61C 19/05
433/69
4,932,867 A * 6/1990 Ueno ..................... A61B 5/228
433/68
(Continued)

FOREIGN PATENT DOCUMENTS

DE     102005015744 A1    10/2006
JP        2011-072733 A     4/2011
(Continued)

OTHER PUBLICATIONS

George et al., Sleep Apnea and Body Position during Sleep, Sleep, Association of Professional Sleep Societies, 11(1):91 (Year: 1987).*
(Continued)

*Primary Examiner* — Michelle J Lee
(74) *Attorney, Agent, or Firm* — Novick, Kim & Lee, PLLC; Jae Youn Kim (57) ABSTRACT

A device for moving a lower jaw forward includes an upper teeth mounting portion on which upper teeth of a human body are mountable, a lower teeth mounting portion on which lower teeth of the human body are mountable, a sensing portion capable of sensing information which determines a movement time of the lower teeth mounting portion, and a driving portion capable of moving the lower teeth mounting portion relative to the upper teeth mounting portion according to a sensing result of the sensing portion. The driving portion includes a power portion which provides a force for moving the lower teeth mounting portion and a driving connection portion which connects the power portion to the lower teeth mounting portion.

7 Claims, 7 Drawing Sheets

(51) Int. Cl.
  *A61B 5/11* (2006.01)
  *A61H 1/00* (2006.01)
  *A61B 7/00* (2006.01)
  *A61B 5/087* (2006.01)

(52) U.S. Cl.
  CPC ............ *A61B 5/4818* (2013.01); *A61B 5/682* (2013.01); *A61F 5/56* (2013.01); *A61H 1/00* (2013.01); *A61B 5/087* (2013.01); *A61B 7/003* (2013.01); *A61H 2201/1246* (2013.01); *A61H 2201/5064* (2013.01); *A61H 2205/026* (2013.01); *A61H 2230/625* (2013.01)

(58) Field of Classification Search
  CPC .... A61H 2201/5058; A61H 2201/5064; A61H 2205/00; A61H 2205/02; A61H 2205/022; A61H 2230/62; A61H 2230/625; A61H 2201/00; A61H 2201/50; A61H 2201/5066; A61H 2230/00; A61F 5/66; A61F 5/56–566; A62B 9/06; A62B 9/00; A62B 9/04; A61C 7/08; A61C 7/36; A61C 7/00; A61C 7/10; A63B 71/085; A63B 71/08–085; A63B 2071/086; A63B 2071/088; A63B 71/00; A61B 5/087; A61B 5/11; A61B 5/1116; A61B 5/4806–4818; A61B 5/4836; A61B 5/682; A61B 7/003; A61B 5/00; A61B 5/08; A61B 5/6813; A61B 5/6814; A61B 7/00
  USPC ......... 128/848, 859; 602/902; 433/140, 214; 600/529
  See application file for complete search history.

(56) References Cited

U.S. PATENT DOCUMENTS

| | | | |
|---|---|---|---|
| 5,409,017 A * | 4/1995 | Lowe | A61C 7/10 |
| | | | 128/848 |
| 5,826,579 A * | 10/1998 | Remmers | A61F 5/566 |
| | | | 128/848 |
| 5,868,138 A | 2/1999 | Halstrom | |
| 5,921,942 A | 7/1999 | Remmers et al. | |
| 5,957,133 A * | 9/1999 | Hart | A61F 5/566 |
| | | | 128/200.26 |
| 6,877,513 B2 * | 4/2005 | Scarberry | A61F 5/566 |
| | | | 128/200.24 |
| 2005/0065560 A1 | 3/2005 | Lee et al. | |
| 2010/0316973 A1 * | 12/2010 | Remmers | A61F 5/566 |
| | | | 433/214 |
| 2011/0036357 A1 * | 2/2011 | Abramson | A61F 5/566 |
| | | | 128/848 |
| 2011/0265801 A1 * | 11/2011 | Cullen | A61F 5/56 |
| | | | 128/848 |
| 2011/0295083 A1 | 12/2011 | Doelling et al. | |
| 2011/0316705 A1 | 12/2011 | Devries et al. | |
| 2012/0240941 A1 * | 9/2012 | Rosenman | A61B 5/682 |
| | | | 128/848 |
| 2014/0261450 A1 * | 9/2014 | Morehead | A61M 16/0816 |
| | | | 128/848 |
| 2015/0216716 A1 | 8/2015 | Anitua Aldecoa | |
| 2016/0324681 A1 * | 11/2016 | Flanagan | A61B 5/682 |
| 2017/0135603 A1 * | 5/2017 | Hanewinkel | A61B 5/087 |
| 2017/0196727 A1 * | 7/2017 | Giridharagopalan | A61B 5/0024 |
| 2018/0085247 A1 * | 3/2018 | Trainor | A62B 9/06 |

FOREIGN PATENT DOCUMENTS

| | | |
|---|---|---|
| KR | 10-1080463 B1 | 11/2011 |
| KR | 10-2013-0045285 A | 5/2013 |
| KR | 20-2013-0005255 U | 9/2013 |
| KR | 10-2014-0148042 A | 12/2014 |
| WO | 2014159236 A2 | 10/2014 |
| WO | 2015/187949 A1 | 12/2015 |
| WO | 2016113629 A1 | 7/2016 |

OTHER PUBLICATIONS

International Search Report for PCT/KR2016/009897.
Examination Report dated Sep. 19, 2018 from Australia Intellectual Property Office in a counterpart Australian Patent Application No. 2016339367.

* cited by examiner

DEVICE FOR MOVING LOWER JAW FORWARD

CROSS-REFERENCE TO RELATED APPLICATION

The present application is a continuation application to International Application No. PCT/KR2016/009897 with an International Filing Date of Sep. 5, 2016, which claims the benefit of Korean Patent Application No. 10-2015-0142680 filed on Oct. 13, 2015 at the Korean Intellectual Property Office, the disclosures of which are incorporated by reference herein in their entirety.

BACKGROUND

1. Field of the Invention

The present invention relates to a device for moving a lower jaw forward.

2. Discussion of Related Art

Generally, when muscles which surround an airway are relaxed during sleeping, the uvula, tonsils, tongue, and the like sag backward. Due to this, the airway may become slightly narrower than when awake, but most people do not have a problem. However, in some people, since the airway becomes seriously narrow so as to prevent air from passing through the airway during sleeping, snoring and obstructive sleep apnea (OSA) occur. As causes of snoring and OSA, there are abnormally small jaws, large tongues or tonsils, partially obstructed airways like uvulae sagging lengthwise, and the like.

For a purpose of relieving the snoring and OSA, a variety of intra-oral devices and methods are used. For example, there is a method of extending a narrow airway using a device which moves a lower jaw forward.

Figure 1:
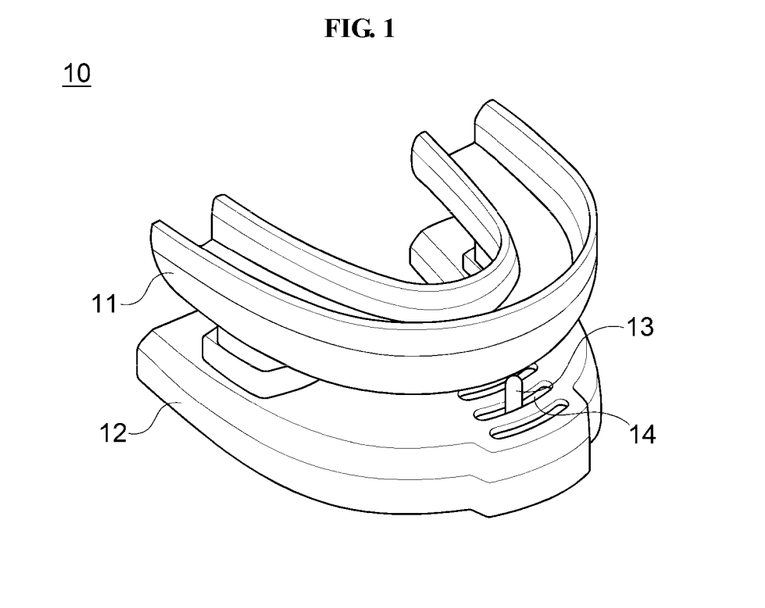
FIG. 1 is a view of a device for moving a lower jaw forward according to a conventional art.

FIG. 1 illustrates a dental appliance for treatment of snoring and OSA according to the conventional art, and a device 10 for moving a lower jaw forward in the dental appliance worn on an oral cavity of a patient to maintain an airway in an upper pharynx of the patient includes an upper member 11 which coincides with a set of teeth of an upper jaw of the patient, a lower member 12 which coincides with a set of teeth of a lower jaw of the patient, a connector 13 extended to be firmly connected to the upper member 11 and a bottom surface extended therefrom, and slots 14 installed spaced apart to be parallel with the lower member 12. The connector 13 is selectively inserted into any one of the slots 14 such that the upper member 11 and the lower member 12 are connected to maintain a state in which the lower member 12 is located in front of the upper member 11 at a relatively protruding position.

SUMMARY

The present invention is directed to providing a device for moving a lower jaw forward, which senses a sleeping posture of a patient who snores and has obstructive sleep apnea while sleeping and is moved according to the sleeping posture.

The present invention is also directed to providing a device for moving a lower jaw forward, which reduces pain caused by wearing the device and decreases drooling.

According to an aspect of the present invention, there is provided a device for moving a lower jaw forward, which includes an upper teeth mounting portion on which upper teeth of a human body are mountable, a lower teeth mounting portion on which lower teeth of the human body are mountable, a sensing portion capable of sensing information which determines a movement time of the lower teeth mounting portion, and a driving portion capable of moving the lower teeth mounting portion relative to the upper teeth mounting portion according to a sensing result of the sensing portion. Here, the driving portion includes a power portion which provides a force for moving the lower teeth mounting portion and a driving connection portion which connects the power portion to the lower teeth mounting portion.

The driving portion may be disposed inside an oral cavity, and the driving connection portion may be a connecting portion which connects the upper teeth mounting portion to the lower teeth mounting portion.

The sensing portion may be located on at least one of the upper teeth mounting portion and the lower teeth mounting portion.

A sleeping posture may include two or more among a supine position, a lateral decubitus position, and a prone position.

The lower teeth mounting portion may be moved forward in the supine position, and the lower teeth mounting portion may return in the lateral decubitus position or the prone position.

The device may further include a controller connected to the sensing portion and the driving portion and configured to control a sensing signal of the sensing portion.

The connecting portion may be formed to be adjustable in length as much as a preset distance.

One end of the connecting portion may be coupled to the lower teeth mounting portion by a hinge, and the other end of the connecting portion may be connected to the driving portion provided at the upper teeth mounting portion. Here, the driving portion may rotate the connecting portion such that the lower teeth mounting portion is movable.

The driving portion may be disposed outside an oral cavity.

The power portion may be a motor capable of injecting air into the driving connection portion. The driving connection portion may include a tube which is a path for the air injected by the motor. The lower teeth mounting portion may include a cylinder in which the air injected by the tube is accommodated.

The sensing portion may be disposed at least one of inside and outside the oral cavity.

The sensing portion may further include a pressure sensor which senses a pressure in the tube.

The upper teeth mounting portion may be connected to a piston which is movable in the cylinder.

A valve may be further disposed in the driving connection portion.

A spring may be disposed at the piston, and the spring may enable the lower teeth mounting portion to return to an original position.

The driving connection portion may include a wire. The power portion may be a motor which provides a force for winding the wire. The wire may move the lower teeth mounting portion according to a posture of the human body.

The device may further include a cylinder connected to the lower teeth mounting portion. Here, the wire may be connected to the cylinder such that the lower teeth mounting portion may move according to movement of the cylinder.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION

Hereinafter, detailed embodiments of the present invention will be described with reference to the drawings. However, they are merely exemplary embodiments and the present invention is not limited thereto.

In describing the present invention, when it is determined that a detailed description on well-known related art may unnecessarily obscure the essentials of the present invention, the detailed description thereof will be omitted. Also, the following terms are defined in consideration of functions thereof in the present invention and may vary according to the intention of a user or an operator, practice, or the like. Accordingly, definitions thereof will be given on the basis of content throughout the specification.

The technical concept of the present invention is determined by the claims, and the following embodiment is merely a means for efficiently explaining the inventive technical concept of the present to one of ordinary skill in the art.

A device 100 for moving a lower jaw forward according to one embodiment of the present invention may be worn to relieve snoring and obstructive sleep apnea.

Figure 2:
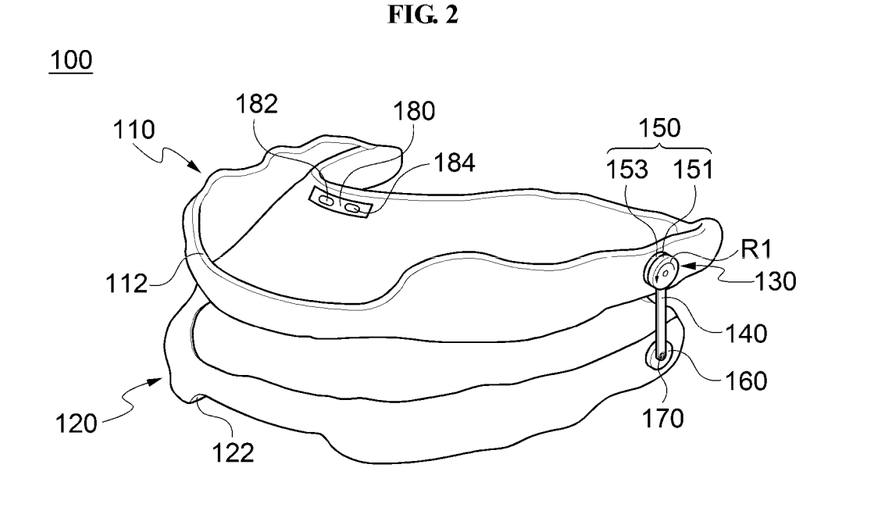
FIG. 2 is a view of a device for moving a lower jaw forward according to one embodiment of the present invention.
Figure 3:
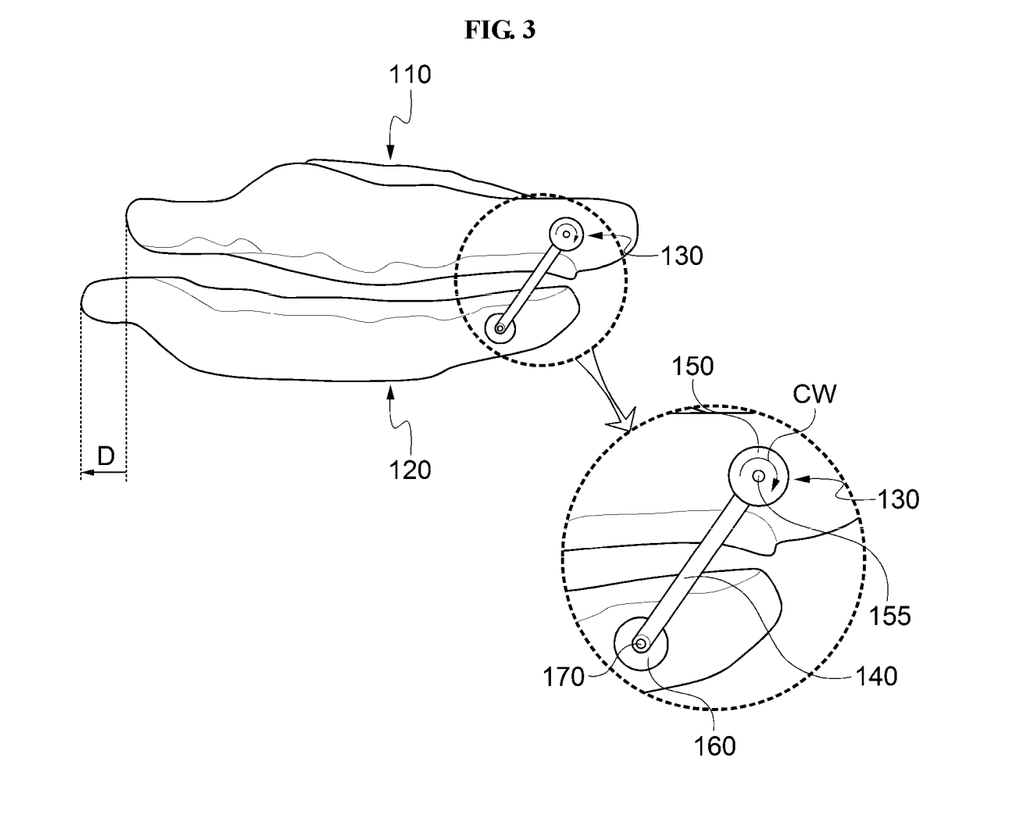
FIG. 3 is a view illustrating a state in which a lower jaw is moved forward by the device for moving a lower jaw forward according to one embodiment of the present invention.

FIGS. 2 and 3 are views illustrating the device 100. The device 100 may include an upper teeth mounting portion 110 on which upper teeth 210 of a human body are mountable, a lower teeth mounting portion 120 on which lower teeth 310 of the human body are mountable, a sensing portion 180 capable of sensing information which determines a point in time for moving the lower teeth mounting portion 120, and a driving portion 190 capable of moving the lower teeth mounting portion 120 relative to the upper teeth mounting portion 110 according to a sensing result of the sensing portion 180.

The driving portion 190 may include a power portion 150 which provides power for moving the lower teeth mounting portion 120 and a driving connection portion 156 which connects the power portion 150 to the lower teeth mounting portion 120.

The driving portion 190 may be disposed inside or outside oral cavity.

The upper teeth mounting portion 110 may include a first insertion groove 112 formed to fit on the upper teeth 210 of a wearer. The first insertion groove 112 may be separately manufactured to custom-fit on a set of the upper teeth 210 of the wearer. When the upper teeth mounting portion 110 is worn on the upper teeth 210, the first insertion groove 112 may cover and come into contact with the upper teeth 210. The lower teeth mounting portion 120 may include a second insertion groove 122 formed to fit on the lower teeth 310 of the wearer. The second insertion groove 122 may be separately manufactured to custom-fit on a set of the lower teeth 310 of the wearer. When the lower teeth mounting portion 120 is worn on the lower teeth 310, the second insertion groove 122 may cover and come into contact with the lower teeth 310.

When the driving portion 190 is present in the oral cavity, one or more connecting portions 130 coupled to at least one of the upper teeth mounting portion 110 and the lower teeth mounting portion 120 may be provided to connect the upper teeth mounting portion 110 to the lower teeth mounting portion 120. Referring to FIG. 2, the connecting portion 130 may include a connecting rod 140 and a hinge fixing portion 160. When the power portion 150 is present outside the oral cavity, the connecting rod 140 may perform a function of the driving connection portion 156 which transfers a force transferred from the power portion 150 to the lower teeth mounting portion 120.

When the driving portion 190 is present in the oral cavity, the power portion 150 may be located on the upper teeth mounting portion 110. The power portion 150 may be coupled to one end of the connecting rod 140 and may rotate the connecting rod 140. The power portion 150 may move the lower teeth mounting portion 120 forward relative to the upper teeth mounting portion 110 (to allow the lower jaw to protrude) according to a sensing result of the sensing portion 180 which will be described below. Here, 'movement' may refer to forward movement or backward movement of the lower teeth mounting portion 120 according to rotation of the power portion 150. For this, the power portion 150 may include a rotating portion 151 fixedly coupled to the connecting rod 140 and a rotational power providing portion 153 coupled to the rotating portion 151 via a rotation transfer shaft 155 and capable of providing rotational power to the rotating portion 151. In addition, the rotational power providing portion 153 may be directly or indirectly coupled to the rotation transfer shaft 155 and may include a bidirectional motor (not shown) capable of rotating the rotation transfer shaft 155. Also, the power portion 150 may include a power source portion (not shown) for driving of a motor. The power source portion may supply power to the motor when it is necessary to move the lower jaw forward according to the sensing result of the sensing portion 180 which will be described below.

A case in which the driving portion 190 is disposed outside the oral cavity will be described below.

Meanwhile, a pain generation amount according to a forward movement amount of the lower jay may vary depending on the wearer who wears the device 100 according to one embodiment of the present invention. Accordingly, a forward movement level of the lower teeth mounting portion 120 for moving the lower jaw forward may be predetermined. The motor may be controlled to rotate the connecting rod 140 to a certain angle, that is, to an angle that allows the lower jaw to move forward to the predetermined forward movement level. For control, the motor may be, for example, a step motor. In addition, to prevent rapid forward movement of the lower jaw caused by rapid rotation of the motor, the power portion 150 may include a decelerator (for example, a reduction gear). Although it has been generally described above that the power portion 150 is provided on the upper teeth mounting portion 110, the power portion 150 is not limited thereto and may be provided on the lower teeth mounting portion 120.

The hinge fixing portion 160 may be rotatably coupled to the other end of the connecting rod 140. The rotational power transferred from the power portion 150, which rotates, may be transferred to a support portion 170 via the hinge fixing portion 160. The hinge fixing portion 160 and the support portion 170 may be directly coupled to the lower teeth mounting portion 120.

The sensing portion 180 may sense a sleeping posture of the human body. The sensing portion 180 may be located on at least one of the upper teeth mounting portion 110 and the lower teeth mounting portion 120. In the present invention, the sensing portion 180 located on the upper teeth mounting portion 110 will be described. The to sensing portion 180 may include a posture sensor 182 which senses the sleeping posture. In addition, the sensing portion 180 may include a snoring sensor 184 which senses a snoring or sleep apnea state.

First, the posture sensor 182 may sense a sleeping posture of the wearer who wears the device 100. The sleeping posture may include two or more of a supine position, a lateral decubitus position, and a prone position. In addition, the device 100 according to the embodiment may also sense a particular sleeping posture according to a sleep disorder level of the wearer. The posture sensor 182 may include one or more of a gyro sensor, an acceleration sensor, a tilt sensor, and the like. The snoring sensor 184 may sense a snoring or sleep apnea state of the wearer who wears the device 100.

The snoring sensor 184 may be a sensor capable of sensing an air flow which passes through a narrowed airway or sensing an external sound such as snoring and the like. When snoring or obstructive sleep apnea occurs, the snoring sensor 184 may sense an irregular or abnormal air flow and may allow the posture sensor 182 or the driving portion 190 to operate. That is, when the wearer who wears the device 100 sleeps without snoring or obstructive sleep apnea, the lower teeth mounting portion 120 is not fixed to the upper teeth mounting portion 10 and remains in a freely relative movement state. When the snoring sensor 184 senses a sleep disorder, the driving portion 190 and the posture sensor 182 operate such that the device 100 according to the embodiment may function.

The sensing portion 180 may include an oxygen saturation sensor. The oxygen saturation sensor may be a sensor capable of sensing oxygen saturation from human body parts including lips (a mouth and lips), gums, and the like. When obstructive sleep apnea occurs, the oxygen saturation sensor may detect a reduction in an oxygen supply amount in the human body and allow the driving portion 190 to operate. Also, a level of how smoothly oxygen is supplied to the human body may be determined by wearing the device 100.

When the driving portion 190 is present outside the oral cavity of the wearer and the device 100 is an air pump type, the sensing portion 180 may include a pressure sensor (not shown) which senses a pressure of air in a tube 156a as well as the sleeping posture of the wearer. In the case of the air pump type, the power portion 150 operates such that the pressure of air in the tube 156a may increase. As the pressure of air increases, a large amount of air may flow into a cylinder 123. Also, as the large amount of air flows into the cylinder 123, the cylinder 123 may be moved further forward. Accordingly, the pressure sensor may be disposed in the tube 156a and may transmit a signal to a controller (not shown) to adequately adjust the pressure in the tube. That is, when the pressure in the tube 156a increases such that the lower jaw is moved sufficiently forward, the operation of the power portion 150 may be stopped and the pressure in the tube 156a may be uniformly maintained. Also, when a reduction in snoring is detected by the snoring sensor and the like or it is necessary to move the lower jaw back to its original position, a valve may be opened to decrease the pressure in the tube 156a.

The sensing portion 180 may be disposed at least one of the inside and outside of the oral cavity. When being disposed outside the oral cavity, the sensing portion 180 may be disposed in not only the driving connection portion 156 but also a separate space and may sense a movement time of the lower teeth mounting portion 120 through short-distance communication such as Bluetooth and the like. The sensing portion 180 may not refer to a single sensor. Several types of sensors may be included, and purposes of the sensors may be different from each other. According to the different purposes of the sensors, the sensors may be arranged in different locations.

FIG. 3 is a view illustrating a state in which the lower teeth mounting portion 120 has been moved forward when the driving portion 190 of the device 100 is present inside the oral cavity. FIG. 3 illustrates a state in which the connecting portion 130 has moved the lower teeth mounting portion 120 forward by a predetermined distance D. When the connecting portion 130 is rotated and moves the lower teeth mounting portion 120, the lower teeth mounting portion 120 may approach the upper teeth mounting portion 110. In this case, the wearer may feel discomfort, and to prevent this, the connecting rod 140 may be formed to be stretchable. For example, the connecting rod 140 may include a cylinder or a multi-stage-withdrawable structure.

When snoring and obstructive sleep apnea occur during sleeping, as shown in FIG. 3, the lower teeth mounting portion 120 may be moved forward (to allow the lower jaw to protrude). The snoring and the obstructive sleep apnea may be sensed by the above-described snoring sensor 184. The snoring sensor 184 may enable the posture sensor 182 or the driving portion 190 to operate. The posture sensor 182 may sense a supine position, a lateral decubitus position, a prone position, and a particular sleeping posture and may enable the driving portion 190 to operate. For example, when the posture sensor 182 senses a supine sleeping posture, the power portion 150 may rotate the connecting rod 140 clockwise (a CW direction in FIG. 3). Accordingly, the lower teeth mounting portion 120 may be moved forward. In a state in which the lower teeth mounting portion 120 has been moved forward, unless the wearer changes a sleeping posture to a lateral decubitus position or a prone position, the lower teeth mounting portion 120 may remain in the advanced state. That is, the rotational power providing portion 153 provides power for continuously maintaining the advanced state of the lower teeth mounting portion 120 or a position of a shaft of the motor is fixed to restrict additional rotation of the connecting rod 140 such that a position of the lower teeth mounting portion 120 may be fixed relative to the upper teeth mounting portion 110. For this, the posture sensor 182 may sense the sleeping posture of the wearer and may transmit a signal of a sensing result thereof to the controller. The controller may be electrically connected to the sensing portion 180 and the driving portion 190. The sensing portion 180 and the driving portion 190 may be electrically connected to the controller in a wired or wireless manner. In the case of the wired connection, a connecting line (not shown) may be embedded in the upper teeth mounting portion 110 of FIG. 2 so as not to be exposed. Also, in the case of wireless connection, a variety of wireless communication means such as Bluetooth, infrared communication, and the like may be used. Meanwhile, the controller may be located in a sleeping place spaced apart from the wearer who wears the device 100 as well as formed in the device 100. In this case, the controller may wirelessly receive a sensing signal and may wirelessly transmit a control signal (a driving signal for the driving portion 190) to the power portion for driving the driving portion 190. Accordingly, the lower teeth mounting portion 120 may be moved forward. The airway near a pharynx is maintained in an opened state by the advanced lower teeth mounting portion 120 expanded to make an airflow in the airway smooth. Accordingly, unlike a conventional case in which lower teeth are moved forward independently of a sleeping posture such that discomfort in a temporomandibular joint or tooth is caused, the lower jaw may be moved forward depending on the sleeping posture of the wearer.

That is, when the wearer who wears the device 100 changes the sleeping posture from the supine position to the lateral decubitus position or prone position, the lower teeth mounting portion 120 may return to an initial position relative to the upper teeth mounting portion 110. By this, when the wearer sleeps in a lateral decubitus position or a prone position, a force is not applied to the lower teeth mounting portion 120 or the upper teeth mounting portion 110 such that temporomandibular joint pain of the wearer may be relieved.

When the device 100 operates, the lower teeth mounting portion 120 may not constantly remain in the advanced state. Even when a change does not exist for a certain period of time, the lower jaw may be retracted at certain time intervals. This is because feelings of fatigue and pain of the wearer may be increased when the lower jaw constantly remains in the advanced state while the wearer is sleeping. The above-described certain time intervals may be preset by the wearer. Otherwise, a provider of the device 100 according to one embodiment of the present invention may previously input intervals to the device 100 as time for minimizing stress on the wearer. That is, while the wearer sleeps, the lower teeth mounting portion 120 is retracted at certain time intervals to help the wearer to sleep well.

Figure 4:
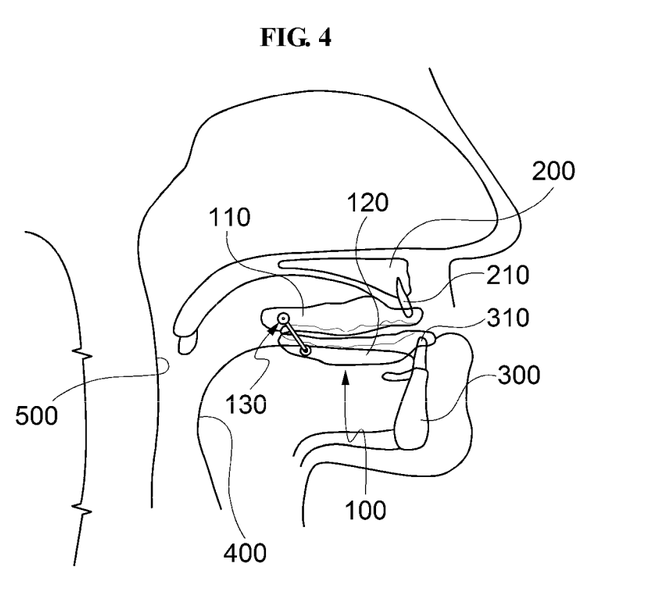
FIG. 4 is a view illustrating a state in which the device for moving a lower jaw forward according to one embodiment of the present invention is worn.

FIG. 4 is a view illustrating a state in which the device 100 according to one embodiment of the present invention is worn in the oral cavity. The wearer wears the device 100, the sensing portion 180 senses the wearing, and the driving portion 190 is driven such that a lower jaw 300 of the wearer may protrude forward with respect to an upper jaw 200. Accordingly, a rear side of a tongue 400 may be moved forward to be spaced apart from a pharynx wall surface 500 therebehind such that an airway remains in an opened state to relieve snoring and obstructive sleep apnea of the wearer who is sleeping. Meanwhile, for a wearer who has an intermittent sleep disorder, the device 100 according to one embodiment of the present invention may include the separate snoring sensor 184. In this case, only when the snoring sensor 184 senses a sleep disorder, the posture sensor 182 may sense a sleeping posture of the wearer and the device 100 according to one embodiment of the present invention may be operated.

Figure 5:
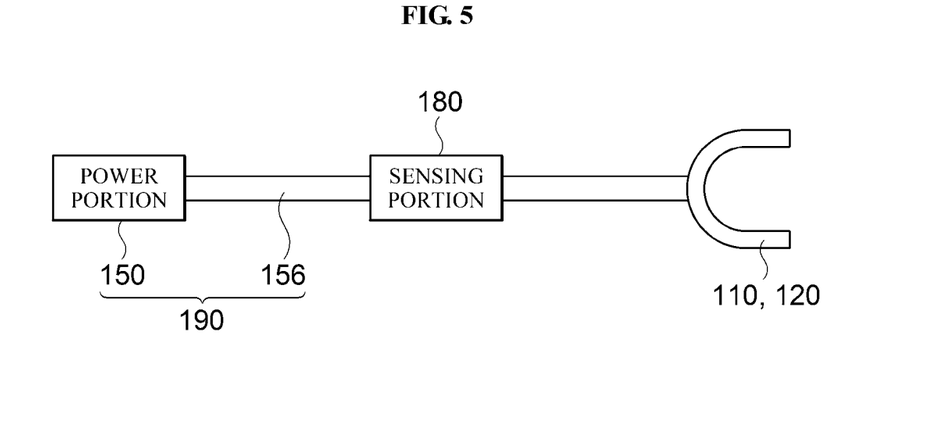
FIG. 5 is a view illustrating components of the device for moving a lower jaw forward according to one embodiment of the present invention.

FIG. 5 is a view illustrating a structure of the device 100 according to one embodiment of the present invention when the driving portion 190 of the device 100 is present outside the oral cavity.

The driving portion 190 may include the power portion 150 which provides power for moving the lower teeth mounting portion and the driving connection portion 156 which connects the power portion 150 to the lower teeth mounting portion 120.

In the power portion 150, a motor varying according to the type of the device 100 according to one embodiment of the present invention may be disposed. When the device 100 is a manual air pump type, the motor may inject air into the driving connection portion 156 to increase a pressure of the air.

On the other hand, when the device 100 according to one embodiment of the present invention is a wire type, the power portion 150 may be a step motor to prevent the wearer from feeling pain due to an excessive force being applied at a time when a wire 156b is pulled, but is not limited thereto.

In describing the embodiment of the present invention, performance properties and effects of the air pump type and the wire type will be described below.

Figure 6:
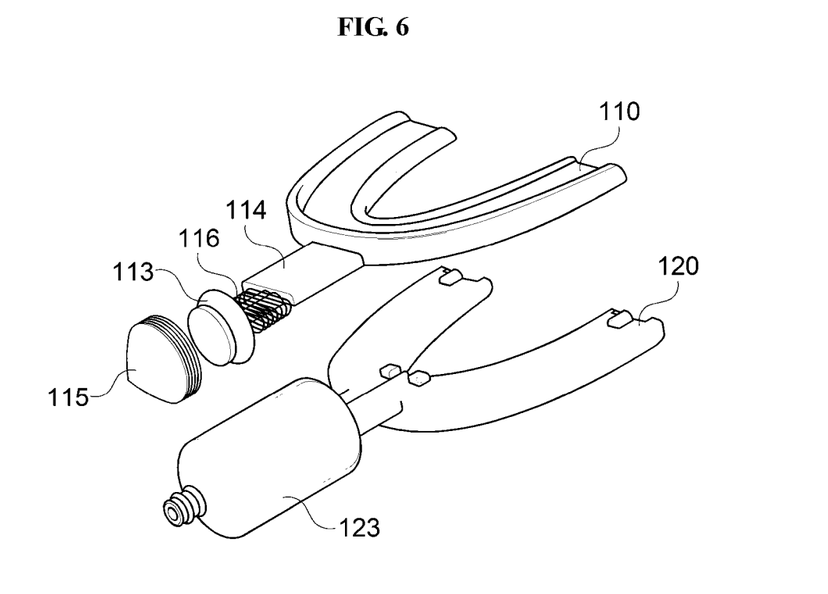
FIG. 6 is an exploded perspective view illustrating an upper teeth mounting portion and a lower teeth mounting portion of the device for moving a lower jaw forward according to one embodiment of the present invention.
Figure 7A:
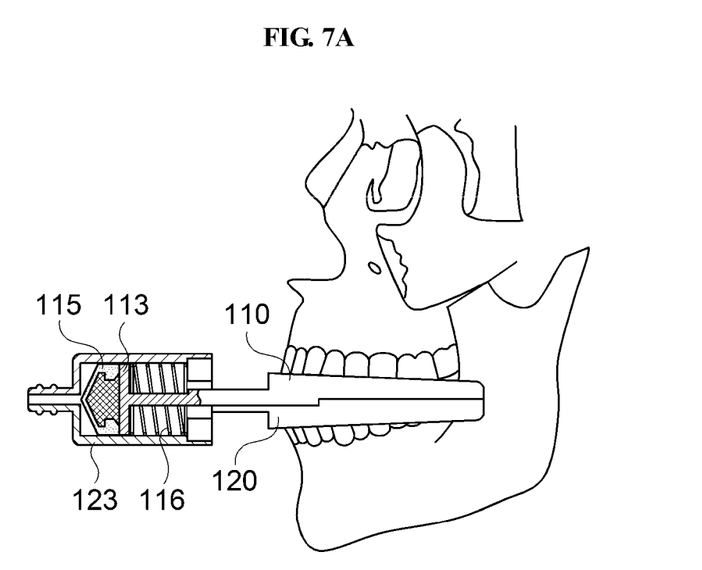
FIGS. 7A and 7B are views illustrating a state in which the device for moving a lower jaw forward according to one embodiment of the present invention is worn.
Figure 7B:
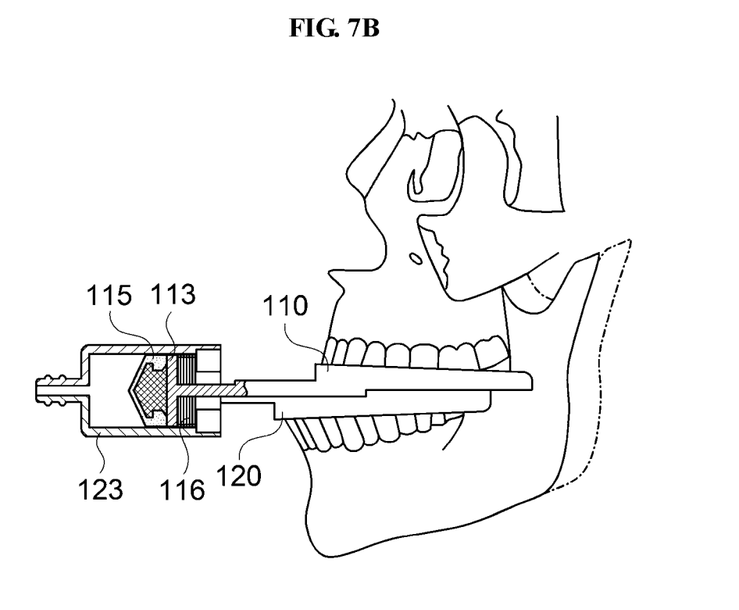

FIG. 6 is an exploded perspective view illustrating the upper teeth mounting portion and the lower teeth mounting portion of the device for moving a lower jaw forward according to one embodiment of the present invention. FIGS. 7A and 7B are views illustrating a state in which the device 100 according to one embodiment of the present invention is worn. FIGS. 7A and 7B may illustrate an example of the air pump type device 100 in which the driving portion 190 is disposed outside the oral cavity.

The upper teeth mounting portion 110 may be integrally connected to a piston 113 by a piston rod 114. The upper teeth mounting portion 110 may be connected to one end of the piston rod 114 as described above, and an elastic member 115 may be connected to one end of the piston 113. The elastic member 115 may be a cap made of a rubber material. A spring 116 may be disposed outside the piston rod 114, and a shape of the piston rod 114 may be formed to fix the spring 116. The piston 113 connected to the upper teeth mounting portion 110 may prevent the upper teeth mounting portion 110 from being moved by power provided by the power portion 150. That is, the piston 113 may fix an upper side of the oral cavity and may perform as a support for allowing a lower side of the oral cavity to be moved forward.

The lower teeth mounting portion 120 may be integrally connected to the cylinder 123. The cylinder 123 may allow the lower teeth mounting portion 120 to be moved forward by the power provided by the power portion 150. As the cylinder 123 moves forward, the spring 116 disposed outside the piston rod 114 may be compressed. The spring 116 may be compressed to provide a restoration force to move the cylinder 123 to a neutral position. Accordingly, the compressed spring 116 may return to an original state and may move the cylinder 123 to the neutral position when the power provided by the power portion 150 is removed.

In the case of the air pump type, the driving connection portion 156 may include the tube 156a. The tube 156a may move air to the cylinder 123 using the power provided by the power portion 150. The air may be injected into the cylinder 123 through the tube 156a. Also, since it is necessary to remove the air injected into the cylinder 123 for moving to the neutral position when the lower teeth mounting portion 120 has been moved forward, a valve 157 may be disposed on the tube 156a. It is possible to adjust a pressure of the air which flows into the tube 156a using the valve 157.

In the case of the wire type, the driving connection portion 156 may include the wire 156b instead of the tube 156a. The power portion 150 and the cylinder 123 may be connected through the wire 156b.

Figure 8:
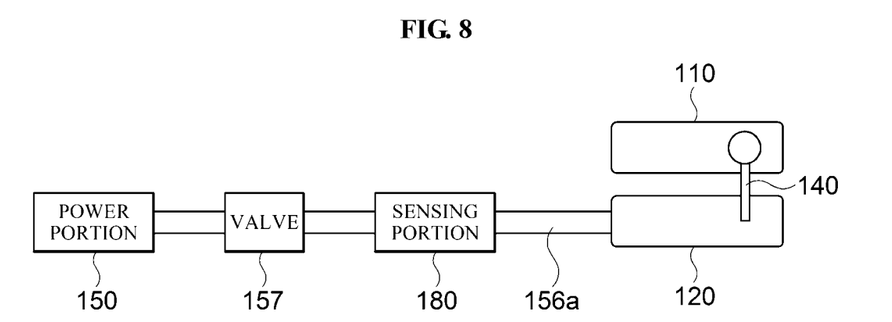
FIG. 8 is a view illustrating a case in which the device for moving a lower jaw forward according to one embodiment of the present invention is an air pump type.

FIG. 8 is a view illustrating the air pump type of the device 100 according to one embodiment of the present invention. FIG. 8 may illustrate an example of the air pump type device 100 in which the driving portion 190 is disposed outside the oral cavity.

As described above, the power portion 150 of the driving portion 190 may be a pump motor. Also, the tube 156a, which is a path for air, may be disposed as the driving connection portion 156, and the valve 157 may be disposed for decreasing a pressure in the tube 156a. The sensing portion 180 may include a pressure sensor and a 3-axis sensor. Here, the connecting rod 140 which connects the upper teeth mounting portion 110 and the lower teeth mounting portion 120 to each other may be included. However, in this case, unlike the driving portion 190 being disposed inside the oral cavity, the connecting rod 140 and the driving connection portion 156 may be separate components.

The air pump type may be operated in a following sequence. However, not limited to the following sequence, necessary steps may be further included in the sequence within a range easily available to those skilled in the art.

First, the driving portion 190 may be operated. The operating of the driving portion 190 may mean that power is supplied to the power portion 150 such that the pressure of air in the tube 156a may be increased. As the pressure of air increases, the air may be injected into the cylinder. As the air is injected, an internal space may be expanded due to an internal pressure of the cylinder 123. Here, a force of pressure may be applied in every direction except an inlet part through which the air is injected. The upper teeth mounting portion 110 connected to the piston 113 to which the elastic member 115 is attached may support the entire teeth. By this, the lower teeth mounting portion 120 may be moved forward. The lower teeth mounting portion 120 moves forward such that the spring 116 may be compressed. To allow the lower jaw to return to a neutral position, the valve 157 is opened to discharge the air such that the pressure in the cylinder 123 may be decreased. As the pressure in the cylinder 123 decreases, the restoration force of the spring 116 acts such that the cylinder 123 and the lower teeth mounting portion 120 may move to the neutral position.

Figure 9:
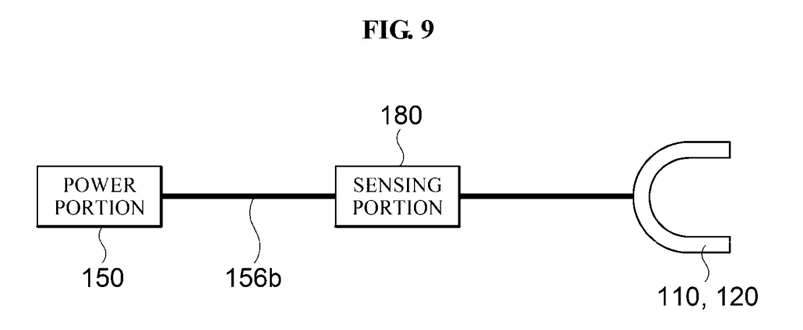
FIG. 9 is a view illustrating a case in which the device for moving a lower jaw forward according to one embodiment of the present invention is a wire type.

FIG. 9 is a view illustrating a case in which the device 100 according to one embodiment of the present invention is the wire type. When the device 100 is the wire type, the device may operate in a following sequence. Like the air pump type, adequate steps may be further included within a range easily available to those skilled in the art.

In the case of the wire type, the power portion 150 of the driving portion 190 may be a step motor. The driving connection portion 156 may include the wire 156b. The sensing portion 180 may sense a sleeping posture or snoring and may transmit a signal to the controller. When it is necessary to move the lower jaw forward in the case of a supine position and the like, the wire may move toward the power portion 150. On the other hand, when it is necessary to retract the lower jaw to the neutral position in the case of a lateral decubitus position and the like, the wire may move toward the wearer.

The power portion 150 may push the wire 156b to allow the lower jaw to return to an original state but is not limited thereto, and the upper teeth mounting portion 110 may include the spring 116 to provide the restoration force.

Referring to FIGS. 8 and 9, when the driving portion 190 may have more functions when present outside the oral cavity than when present inside. This is because a volume in the oral cavity has a limit and the limitation may limit the size of component. Also, when the driving portion 190 is inside the oral cavity, power provided for moving the lower jaw forward may be not sufficient.

On the other hand, when the driving portion 190 is present outside the oral cavity, the selection of the motor which provides the power for moving the lower jaw forward is relatively free compared to when the driving portion 190 is present inside the oral cavity, and the sensing portion 180 and the like disposed on the driving connection portion 156 may also be freely selected. As the selection becoming free, the sensing portion 180 having more excellent performance may be disposed.

Also, discomfort felt by the wearer may be reduced and noise may be lessened so as not to interrupt sleeping.

Figure 10:
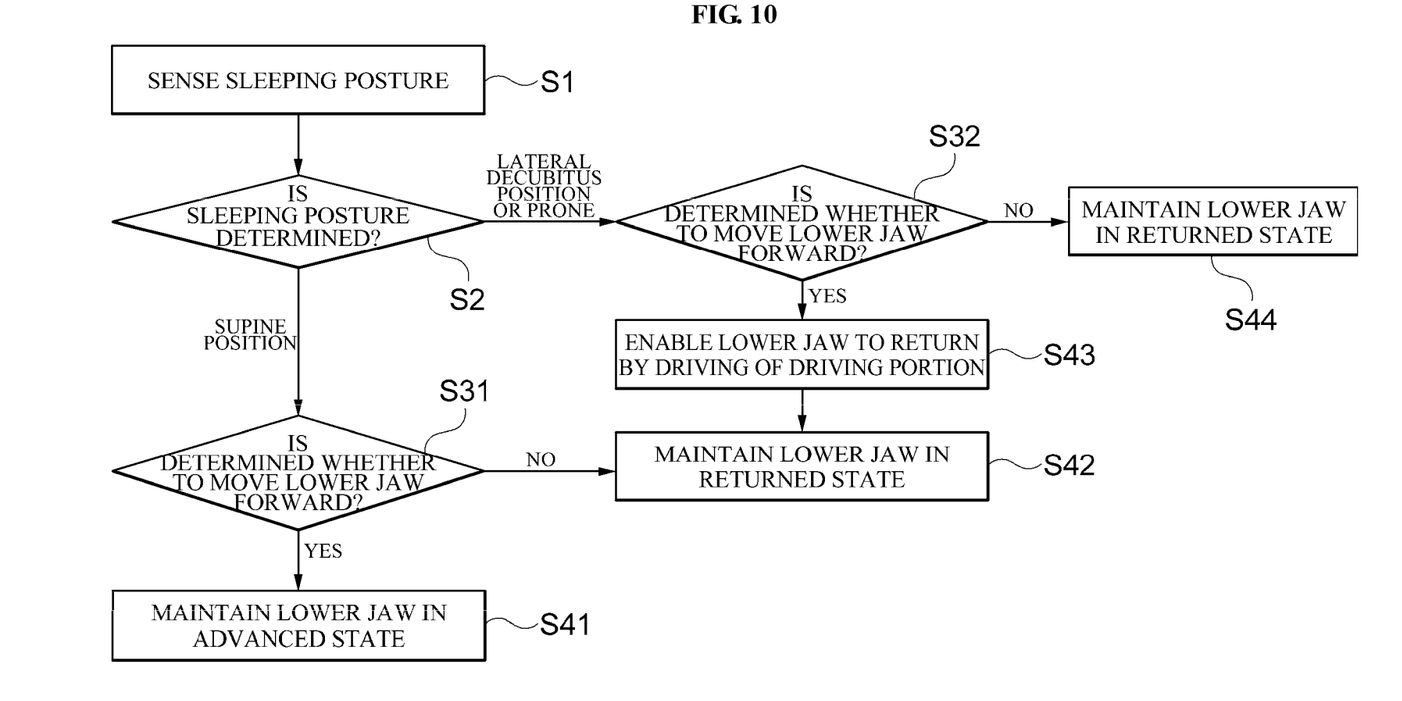
FIG. 10 is a flowchart illustrating operations of the device for moving a lower jaw forward according to one embodiment of the present invention.

FIG. 10 is a view illustrating an example of the overall operating principle of the device according to one embodiment of the present invention. In step S1, a sleeping posture of a wearer who wears the device 100 may be sensed. In step S2, the sleeping posture may be determined by the sensing portion 180 located in the device 100. In step S31, when the sleeping posture is determined as a supine position, it may be determined whether to move a lower jaw forward. In step S41, when the lower jaw has been moved forward, the lower jaw may be maintained in an advanced state. Otherwise, in step S42, the lower jaw may be moved forward by driving the driving portion 190. In step S32, when the sleeping posture is determined as a lateral decubitus position or a prone position, it may be determined whether to move the lower jaw forward. In step S43, when the lower jaw has been moved forward, the lower jaw may be returned due to driving of the driving portion. In step S44, when the lower jaw has returned, the lower jaw may be maintained in a returned state.

FIG. 10 exemplarily illustrates an algorithm with respect to the sleeping posture and the present invention is not limited thereto. As described above, it may be determined through information sensed by the snoring sensor, the oxygen saturation sensor, and the like whether to move the lower jaw forward. It may be determined by comprehensively determining the information sensed by each of the sensors whether to move the lower jaw forward.

For example, even when the sleeping posture is a lateral decubitus position, snoring becomes serious depending on the wearer's condition. In this case, forward movement of the lower jaw may be performed through snoring sounds sensed by the snoring sensor. That is, a priority of each of the sensors may be determined to determine whether to move the lower jaw forward or whether to move the lower jaw forward may be determined by comprehensively considering the information sensed by each of the sensors. The device 100 may be arbitrarily preset by the wearer and may be freely changed to be used. Accordingly, the device may not be uniformly applied to all people and may be personally optimized to be used.

According to embodiments of the present invention, a device for moving a lower jaw forward senses a sleeping posture of a patient who snores and has obstructive sleep apnea while sleeping and is moved according to the sleeping posture.

Also, a device for moving a lower jaw forward reduces pain caused by wearing the device and decreases drooling.

Also, a device for moving a lower jaw forward is capable of providing an adequate force for moving the lower jaw forward by a driving portion disposed outside an oral cavity.

Also, an air pump type device for moving a lower jaw forward using a pressure of air or a wire type device for moving a lower jaw forward by winding a wire can be provided.

Although exemplary embodiments of the present invention have been described in detail, it will be understood by one of ordinary skill in the art that the above-described embodiments may be variously modified without departing from the scope of the present invention. Therefore, the scope of the present invention should not be limited to the above-described embodiments and should be determined by the following claims and equivalents thereof.

What is claimed is:

1. A device for moving a lower jaw forward, comprising:
   an upper teeth mounting portion on which upper teeth of a human body are mountable;
   a lower teeth mounting portion on which lower teeth of the human body are mountable;
   a sensing portion having a posture sensor capable of sensing a sleeping posture of the human body;
   and a driving portion capable of moving the lower teeth mounting portion relative to the upper teeth mounting portion according to information on the sleeping posture transmitted from the sensing portion,
   wherein the driving portion includes a power portion configured to provide a force for moving the lower teeth mounting portion and a connection portion connecting the power portion to the lower teeth mounting portion,
   wherein, when the sensing portion senses changes of the sleeping posture, the driving portion is configured to move the lower teeth mounting portion according to the changes of the sleeping posture,
   wherein the connection portion includes a connecting rod rotatably attached at each end to the upper teeth mounting portion and the lower teeth mounting portion, respectively, and
   wherein the power portion includes a rotating portion fixedly coupled to the connecting rod and a motor coupled to the rotating portion via a rotation transfer shaft and capable of providing rotational power to the rotating portion, such that the lower teeth mounting portion is moved relative to the upper teeth mounting portion by rotation of the connecting rod to change an angle of the connecting rod with respect to an occlusal surface of the upper teeth mounting portion.

2. The device of claim 1, wherein the driving portion is configured to be disposed inside an oral cavity.

3. The device of claim 2,
   wherein the sleeping posture comprises two or more of a supine position, a lateral decubitus position, and a prone position.

4. The device of claim 3, wherein the lower teeth mounting portion is configured to move forward in the supine position, and
   the lower teeth mounting portion is configured to return in the lateral decubitus position or the prone position.

5. The device of claim 2, wherein the sensing portion is located on at least one of the upper teeth mounting portion and the lower teeth mounting portion.

6. The device of claim 2, further comprising a controller configured to control a sensing signal of the sensing portion.

7. The device of claim 2, wherein the connection portion is adjustable in length.

* * * * *